United States Patent [19]
Doe, Jr.

[11] Patent Number: 4,677,149
[45] Date of Patent: Jun. 30, 1987

[54] NORBORNENE DERIVATIVES OF PHENOLS

[75] Inventor: Lester A. Doe, Jr., Newtown, Conn.

[73] Assignee: R. T. Wanderbilt Company, Inc., Norwalk, Conn.

[21] Appl. No.: 940,687

[22] Filed: Dec. 11, 1986

[51] Int. Cl.⁴ .................. C07C 43/178; C08K 5/13
[52] U.S. Cl. .................. 524/324; 568/659
[58] Field of Search ........... 524/324, 340, 928; 568/659, 820

[56] References Cited

U.S. PATENT DOCUMENTS

| | | | |
|---|---|---|---|
| 2,537,636 | 1/1951 | Kitchen | 524/326 |
| 2,581,907 | 1/1952 | Smith et al. | 524/326 |
| 2,581,917 | 1/1952 | Kitchen | 568/632 |
| 2,628,953 | 2/1953 | Newby | 524/925 |
| 2,954,345 | 9/1960 | Filbey | 524/326 |
| 3,169,941 | 2/1965 | Alt et al. | 524/925 |
| 3,180,850 | 4/1965 | Schooten et al. | 524/324 |
| 3,233,009 | 2/1966 | Carlick et al. | 568/820 |
| 3,489,804 | 1/1970 | O'Shea | 524/326 |
| 3,492,330 | 1/1970 | Trecker et al. | 568/632 |
| 3,563,947 | 2/1971 | Gruber | 524/285 |
| 3,814,727 | 6/1974 | Hartmann et al. | 524/191 |
| 4,088,630 | 5/1978 | Roos et al. | 260/45.8 |
| 4,427,817 | 1/1984 | Brück et al. | 524/367 |
| 4,548,976 | 10/1985 | De Roche et al. | 524/324 |

FOREIGN PATENT DOCUMENTS 950554 2/1964 United Kingdom .

Primary Examiner—Veronica P. Hoke
Attorney, Agent, or Firm—Rasma B. Balodis

[57] ABSTRACT

Novel phenols substituted by at least one 5-norbornen-2-ylmethoxymethyl group and optionally, by methyl or t-butyl groups are used as nondiscoloring antiozonants and antioxidants in chloroprene polymers.

8 Claims, No Drawings

NORBORNENE DERIVATIVES OF PHENOLS

BACKGROUND OF THE INVENTION

The present invention concerns novel norbornene derivatives of phenols and their use in polymeric compositions having improved ozone resistance.

Elastomeric vulcanizates are known to develop surface cracks when exposed to atmospheric influences and certain mechanical conditions. Such crack formation is caused by the presence of ozone. Elastomeric polychoroprene vulcanizates are particularly susceptible to ozone attack if subjected to mechanical stress and flex. Cracks are formed more readily at elevated temperatures.

To prevent crack formation, it is necessary to incorporate an antiozonant into the polymer composition.

It is known that polychloroprene vulcanizates may be protected against ozone-cracking by norbornene-type antiozonants. U.S. Pat. No. 3,563,947 discloses dinorbornene derivatives of alkyl-substituted benzenes and of other divalent organic radicals. Enol ethers of norbornene are described in U.S. Pat. No. 3,814,727 and acetals or ketals in U.S. Pat. No. 4,427,817.

However, various functionally active antiozonants often display adverse effects on the compounded or cured elastomeric article. A particularly undesirable effect is the tendency of polychloroprene compositions to develop undesirable color or staining. Only a few nondiscoloring antiozonants are commercially available. Now certain novel norbornene derivatives have been discovered that possess antiozonant and antioxidant activity as well as nondiscoloring properties in polychloroprene.

SUMMARY OF THE INVENTION

According to the present invention there are provided novel compounds of the formula

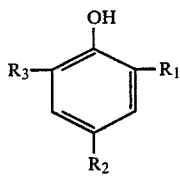

wherein the substitutents $R_1$, $R_2$ and $R_3$ represent H, methyl, t-butyl and 5-norbornen-2-ylmethoxymethyl group represented by the formula

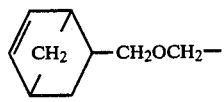

provided that at least one of the sustituents is the 5-norbornen-2-ylmethoxymethyl group.

The invention further provides neoprene compositions having improved ozone and oxygen resistance.

DETAILED DESCRIPTION OF THE INVENTION

The novel compounds of the invention may be prepared by reacting about equimolar amounts of 5-norbornene-2-methanol, formaldehyde and a phenol in the presence of an acid catalyst. The reaction may be represented by the following reaction scheme.

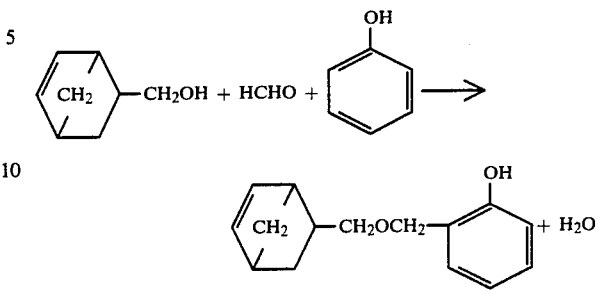

The acid catalyst may be selected from strong acids such as p-toluenesulfonic acid, sulfuric acid, hydrochloric acid and phosphoric acid.

The reaction may be conducted in the presence of an inert solvent. The solvent may be selected from aromatic or aliphatic hydrocarbons as for example toluene, xylene and hexane. The reaction temperature will depend upon the solvent used, that is, upon the azeotropic reaction mixture formed.

The norbornene derivatives of the invention are effective antiozonants. When incorporated into elastomeric polychloroprene (neoprene), the vulcanizates display good resistance to ozone cracking without discoloration. In addition the alkyl substituted derivatives display antioxidant properties.

The homopolymers and copolymers of chloroprene are well known in the art and are commercially available. Representative monomers which can be copolymerized with chloroprene include aliphatic conjugated diolefins and other compounds having a double bond such as vinyl acetate, acrylonitrile, acrylic and methacrylic acid and their esters.

The novel compounds may be added to the polymers in sufficient quantity to protect against ozone degradation, for example, between 0.1 and 6.0 percent by weight and preferably between 0.3 and 3.0 percent by weight based on hundred parts by weight of polymer.

The polychloroprene compositions may contain compounding additives necessary for curing, namely metal oxides and accelerators. The metal oxides may be selected from zinc oxide, magnesium oxide, lead oxide and mixtures thereof. Accelerators may include, among others, N, N-di-o-tolylguanidine, alkyl-substituted thioureas, tetramethylthiuram disulfide, N-t-butyl-2-benzothiazolesulfenamide and binary systems consisting of thiadiazine and metal dithiocarbamate secondary accelerators. Other ingredients may be compounded with polychloroprene to improve its processing properties and physical characteristics. Among others, the following are applicable: antioxidants, plasticizers, peptizers, fillers, extenders, reinforcing fillers, and lubricants.

Any suitable curing procedure and conditions may be employed in the invention. Two methods, among others, are to press-cure at a temperature of about 138° to 182° C. for about 10 to 120 minutes and to vulcanize continuously at a temperature of about 182° to 204° for about 5 to 150 seconds.

The following examples are submitted to illustrate, but not to limit the scope of the invention. Unless otherwise indicated, all parts and percentages in the specification and claims are based upon weight.

EXAMPLE I

A reactor was charged with 32.8 g (0.20 moles) 2-t-butyl-4-methylphenol, 6.0 g (0.20 moles) formaldehyde, 24.8 g (0.20 moles) 5 norbornene-2-methanol, 110 ml toluene and 0.5 g p-toluenesulfonic acid catalyst. The reaction mixture was refluxed for 1½ hours. About 13.8 ml water was collected by azeotropic distillation. After cooling the reaction mixture, 5 ml of 20% sodium carbonate solution was added to neutralize the catalyst. After stripping, hexane was added and the reaction mixture was filtered.

The yield of the product, 2-(5-norbornen-2-ylmethoxymethyl)-4-methyl-6-t-butylphenol, was 60.6 g.

EXAMPLE II

Rubber specimens were prepared according to the formulations given in Table I.

The antiozonant effect of the compounds of the invention was measured by two tests: the ozone resistance test according to the ASTM Method D-1149-86 and the bent loop ozone cracking test by the ASTM Method D-518-86.

In the ozone resistance method, test specimens measuring 0.4×4.5×4.5 cm press cured at 160° C. for 30 minutes were clamped in a frame in such a way that elongations of 10 to 100 percent were obtained at their surfaces. The stretched specimens were exposed to 100 parts ozone per hundred million parts air. After 14 days stress was measured.

In the bent loop test the difference in stress was measured at 22% elongation after 14 days.

To determine discoloration tendency by the antiozonants, the specimens were exposed to ultraviolet light according to the ASTM Method D-1148-77. Brightness was measured before exposure and after exposure for 25 hours.

To determine antioxidant properties of the compounds, the specimens were aged in test tubes (Al blocks) for 70 hours at 121° C. The physical properties were determined according to ASTM D-865-81 Test Method.

The results compiled in Table I show that the compounds of the invention have good antiozonant properties. Moreover, the compounds do not discolor the cured neoprene specimens.

Specimens containing the norbornene derivatives of the invention also display antioxidant properties in addition to the antiozonant properties discussed above.

The above embodiments and illustrations have shown various aspects of the present invention. Other variations will be evident to those skilled in the art and such modifications are intended to be within the scope of the invention as defined by the appended claims.

TABLE I

|  | 1 | 2 | 3 | 4 | 5 | 6 |
|---|---|---|---|---|---|---|
| Formulation, in parts by weight |  |  |  |  |  |  |
| Neoprene W | 100.0 | 100.0 | 100.0 | 100.0 | 100.0 | 100.0 |
| Magnesium oxide | 4.0 | 4.0 | 4.0 | 4.0 | 4.0 | 4.0 |
| Zinc oxide | 5.0 | 5.0 | 5.0 | 5.0 | 5.0 | 5.0 |
| Stearic acid | 0.5 | 0.5 | 0.5 | 0.5 | 0.5 | 0.5 |
| Titanium dioxide | 10.0 | 10.0 | 10.0 | 10.0 | 10.0 | 10.0 |
| Kaolin clay | 90.0 | 90.0 | 90.0 | 90.0 | 90.0 | 90.0 |
| Plastogen[1] | 5.0 | 5.0 | 5.0 | 5.0 | 5.0 | 5.0 |
| VANAX CPA[2] | 1.5 | 1.5 | 1.5 | 1.5 | 1.5 | 1.5 |
| 4-(5-Norbornen-2-ylmethoxymethyl)-2,6-di-t-butylphenol | — | 2.0 | — | — | — | — |
| 2-(5-Norbornen-2-ylmethoxymethyl)-4-methyl-6-t-butylphenol | — | — | 2.0 | — | — | — |
| 2,4,6-Tris(5-norbornen-2-ylmethoxymethyl)phenol | — | — | — | 2.0 | — | — |
| 2,4-Di(5-norbornen-2-ylmethoxymethyl)-6-methylphenol | — | — | — | — | 2.0 | — |
| 2-(5-Norbornen-2-ylmethoxymethyl)-4,6-di(t-butyl)phenol | — | — | — | — | — | 2.0 |
| Ozone Resistance |  |  |  |  |  |  |
| 10% Elongation | 0 | 0 | 0 | 0 | 0 | 0 |
| 15% Elongation | 10 | 0 | 0 | 0 | 0 | 0 |
| 20% Elongation | 10 | 0 | 0 | 0 | 0 | 0 |
| 50% Elongation | 10 | 0 | 0 | 0 | 0 | 0 |
| 75% Elongation | 10 | 0 | 0 | 0 | 0 | 0 |
| 100% Elongation | 10 | 0 | 0 | 0 | 0 | 0 |
| Bent Loop Ozone Resistance |  |  |  |  |  |  |
| 22% Elongation | 9 | 0 | 0 | 0 | 0 | 0 |
| Brightness |  |  |  |  |  |  |
| Before exposure | 52.1 | 51.6 | 52.1 | 50.9 | 50.8 | 52.1 |
| After exposure for 24 hours | 10.7 | 12.2 | 18.2 | 11.4 | 11.6 | 14.6 |
| Properties after aging for 70 hours at 121° C. |  |  |  |  |  |  |
| Tensile | 1520 | 1400 | 1430 | 1490 | 1570 | 1540 |
| Elongation, Percent | 50 | 80 | 260 | 100 | 100 | 140 |
| Hardness | 85 | 82 | 79 | 84 | 83 | 81 |

[1]Plastogen ®, sulfonic acid type plasticizer, manufactured by King Industries
[2]VANAX ® CPA, dimethylammonium hydrogen isophthalate, manufactured by R. T. Vanderbilt Co.

What is claimed is:
1. A compound of the formula

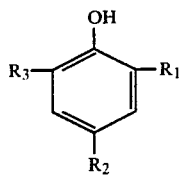

wherein the substituents $R_1$, $R_2$ and $R_3$ represent H, methyl, t-butyl and 5-norbornen-2-ylmethoxymethyl group represented by the formula

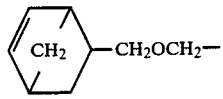

provided that at least one of the substituents is the 5-norbornen-2-ylmethoxymethyl group.

2. The compound according to claim 1 which is 4-(5-norbornen-2-ylmethoxymethyl)-2,6-di-t-butylphenol.

3. The compound according to claim 1 which is 2-(5-norbornen-2-ylmethoxymethyl)-4-methyl-6-t-butylphenol.

4. A composition comprising a chloroprene polymer and a stabilizing amount of a phenolic compound of the formula

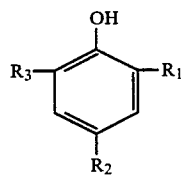

wherein the substituents $R_1$, $R_2$ and $R_3$ represent H, methyl, t-butyl and 5-norbornen-2-ylmethoxymethyl group represented by the formula

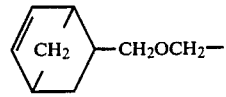

provided that at least one of the substituents is the 5-norbornen-2-ylmethoxymethyl group.

5. The composition according to claim 4 wherein the phenolic compound is 4-(5-norbornen-2-ylmethoxymethyl)-2,6-di-t-butylphenol.

6. The composition according to claim 4 wherein the phenolic compound is 2-(5-norbornen-2-ylmethoxymethyl)-4-methyl-6-t-butylphenol.

7. The composition according to claim 4 wherein the phenolic compound is present in the amount of about 0.1 to 6.0 percent by weight based on hundred parts by weight of polymer.

8. A process for stablizing a chloroprene polymer composition against ozone and oxygen attack which comprises adding to said polymer about 0.1 to 6.0 percent by weight based on hundred parts by weight of polymer of a phenolic compound of the formula

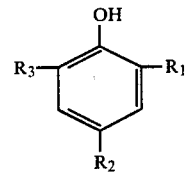

wherein the substituents $R_1$, $R_2$ and $R_3$ represent H, methyl, t-butyl and 5-norbornen-2-ylmethoxymethyl group represented by the formula

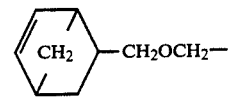

provided that at least one of the substituents is the 5-norbornen-2-ylmethoxymethyl group.

* * * * *

UNITED STATES PATENT AND TRADEMARK OFFICE
CERTIFICATE OF CORRECTION

PATENT NO. : 4,677,149

DATED : June 30, 1987

INVENTOR(S) : Lester A. Doe, Jr.

It is certified that error appears in the above-identified patent and that said Letters Patent are hereby corrected as shown below:

Title page, [73] Assignee:

"R. T. Wanderbilt Company, Inc." should be
------- R. T. Vanderbilt Company, Inc.-----

Signed and Sealed this

Twenty-seventh Day of October, 1987

Attest:

DONALD J. QUIGG

*Attesting Officer*  *Commissioner of Patents and Trademarks*